United States Patent [19]

Widder et al.

[11] 4,247,406

[45] Jan. 27, 1981

[54] INTRAVASCULARLY-ADMINISTRABLE, MAGNETICALLY-LOCALIZABLE BIODEGRADABLE CARRIER

[76] Inventors: Kenneth J. Widder; Andrew E. Senyei, both of 8 E. Pearson St., Chicago, Ill. 60611

[21] Appl. No.: 32,399

[22] Filed: Apr. 23, 1979

Related U.S. Application Data

[63] Continuation-in-part of Ser. No. 820,812, Aug. 1, 1977, abandoned.

[51] Int. Cl.² .................. A61K 9/50; A61K 9/38; G01N 33/16; A61K 43/00
[52] U.S. Cl. .................. 252/62.53; 252/62.54; 424/1; 424/36
[58] Field of Search .................. 252/62.53, 62.54; 424/1, 36

[56] References Cited

U.S. PATENT DOCUMENTS

| | | | |
|---|---|---|---|
| 2,671,451 | 3/1954 | Bolger | 128/260 |
| 2,971,916 | 2/1961 | Schleicher et al. | 252/62.51 |
| 3,057,344 | 10/1962 | Abella et al. | 128/2 |
| 3,190,837 | 6/1965 | Brynko et al. | 252/316 |
| 3,474,777 | 10/1969 | Figge et al. | 128/1.1 |
| 3,663,687 | 5/1972 | Evans | 424/1 |
| 3,725,113 | 4/1973 | Chang | 424/101 X |
| 3,937,668 | 2/1976 | Zolle | 252/316 |
| 4,082,681 | 4/1978 | Takayama et al. | 252/62.1 P |
| 4,107,288 | 8/1978 | Oppenheim et al. | 424/36 |
| 4,108,786 | 8/1978 | Takayama et al. | 252/62.1 P |
| 4,115,534 | 9/1978 | Ithakissons | 424/1 |
| 4,147,767 | 4/1979 | Yapel | 424/22 |

FOREIGN PATENT DOCUMENTS

| | | |
|---|---|---|
| 1351358 | 12/1963 | France . |
| 1468601 | 1/1967 | France . |
| 2326934 | 5/1977 | France . |
| 48-24246 | 7/1973 | Japan . |
| 280825 | 12/1964 | Netherlands . |
| 280826 | 12/1964 | Netherlands . |
| 929401 | 6/1963 | United Kingdom . |

OTHER PUBLICATIONS

Nakamura et al., J. Applied Physics, vol. 42, No. 4, pp. 1320, 1321 (Mar. 1971).
Scheffel et al., J. Nuclea Medicine, vol. 13, No. 7, pp. 498–502 (1972).
Kramer, J. Pharm. Sci., vol. 63, pp. 1646–1647 (10–74).
Takai et al., Chem. Abs., vol. 80, No. 5, Abs. 52392a, 3/74.

*Primary Examiner*—F. C. Edmundson

[57] ABSTRACT

The intravascularly-administrable, magnetically localizable biodegradable carrier comprises microspheres formed from an amino acid polymer matrix with magnetic particles embedded therein. The microspheres can be used for intraarterial administration and capillary level localization and/or release of therapeutic and diagnostic agents, thereby obtaining much more precise targeting of the agents than has heretofore been possible.

12 Claims, 3 Drawing Figures

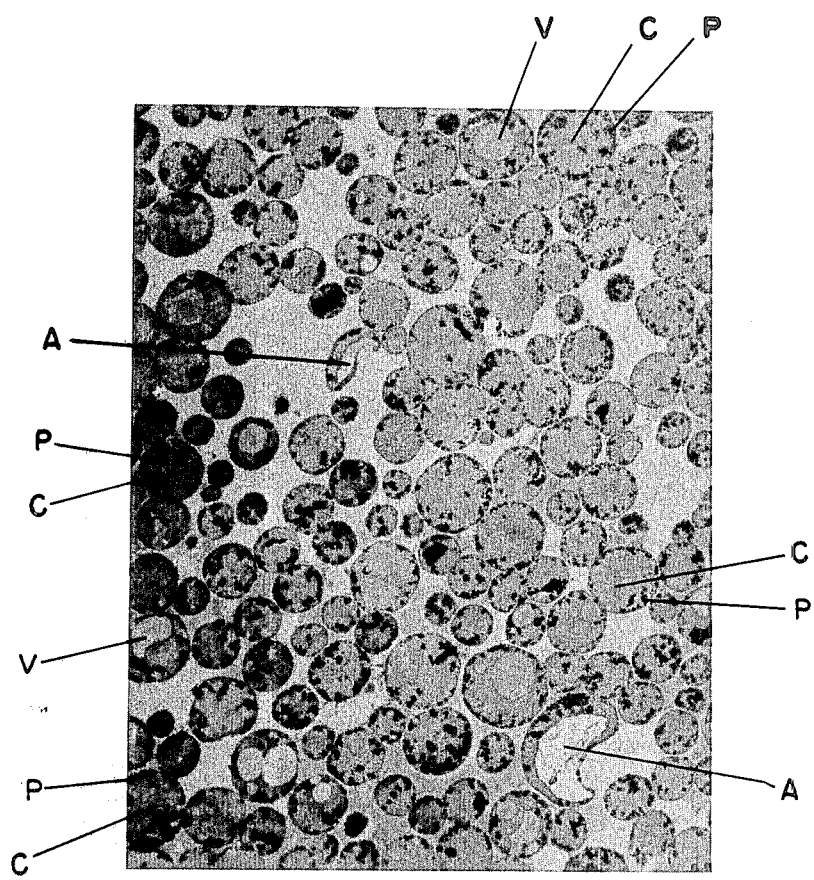

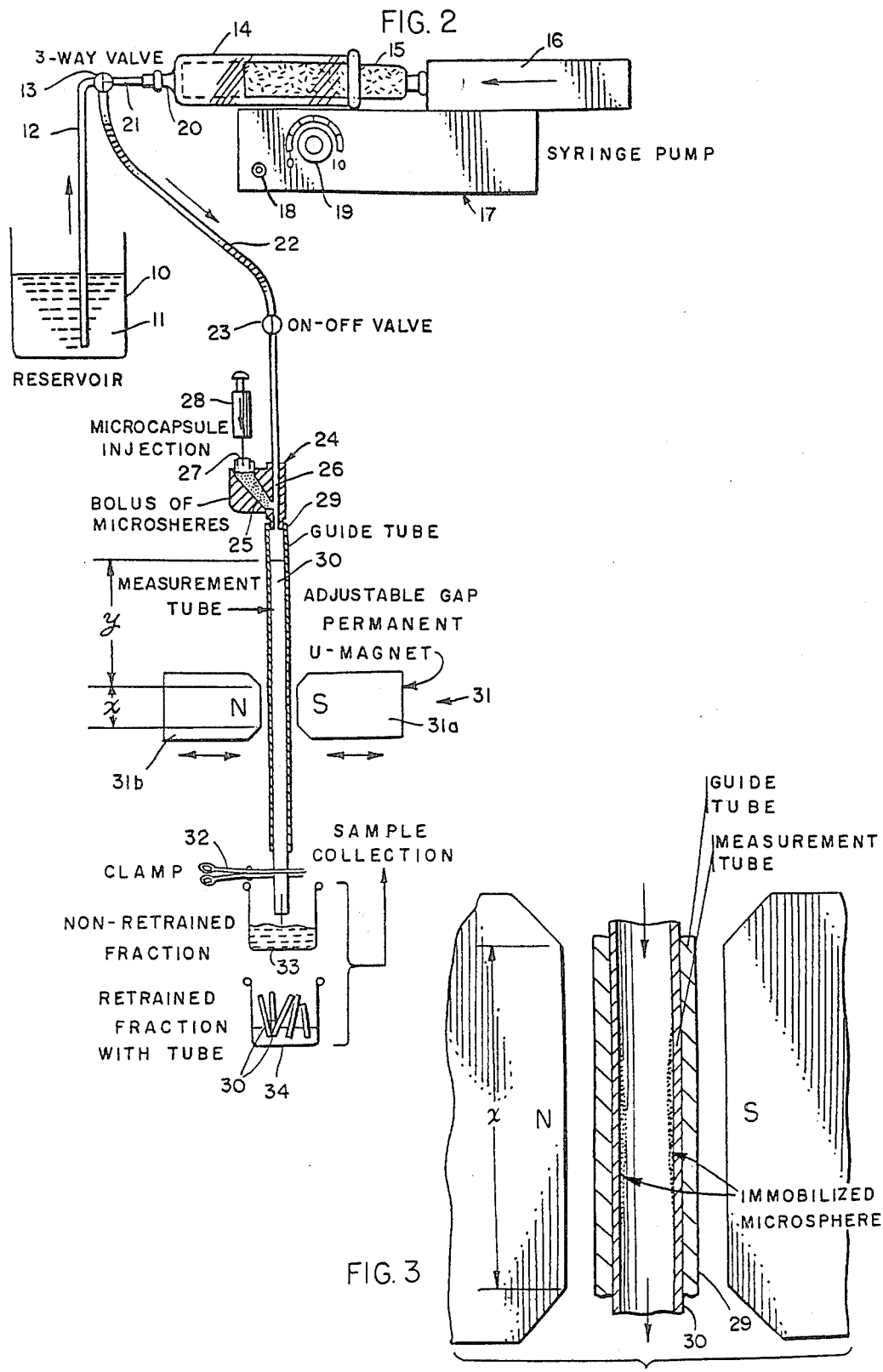

INTRAVASCULARLY-ADMINISTRABLE, MAGNETICALLY-LOCALIZABLE BIODEGRADABLE CARRIER

This application is a continuation-in-part of co-pending application Ser. No. 820,812, filed Aug. 1, 1977, now abandoned.

BACKGROUND AND PRIOR ART

Specific delivery of chemotherapeutic agents to desired target sites with a minimum of systemic side effects constitutes one of the ongoing challenges of chemotherapy. Chemical approaches to such "targeting" depend on biochemical differences between cells, but such differences are more quantitative than qualitative. Thus the drugs administered have activity in areas of the body where activity is not desired. An alternative to chemically mediated targeting is the entrapment of a chemotherapeutic agent in a carrier which can mechanically effect distribution of the drug.

In 1974, Kramer proposed albumin microspheres as vehicles for achieving specificity in drug delivery. J. Pharm. Sci., 63, 1646-1647 (Oct. 1974). Entrapment of the anti-cancer drug mercaptopurine was demonstrated but not specifity of delivery. Kramer did suggest that intravenous administration of the microspheres might result in preferential uptake in such tissues as liver or bone marrow due to non-specific phagocytosis with a possible reduction in required total doses and thereby less systemic side effects. This would still be far short of the desired objective since only diseases of the reticuloendothelial system would be affected. Local compartmentalization of water soluble chemotherapeutic agents at desired target sites, if it could be achieved, would permit administration of much lower doses by largely eliminating systemic dilution of the drug. In addition, many of the adverse side effects that are often the result of systemic distribution could be eliminated. Unfortunately, prior to the present invention, no system of administration has been provided which can effectively deliver therapeutic agents intravascularly to a selected site. Such a system also has value for administration of diagnostic agents.

Freeman et al proposed in 1960 that magnetic iron particles might be used as a means for transporting radiation or some healing chemical to a particular spot in the body, the particles being magnetically directed. J. App. Phys., Supp. Vol. 31, 404S-405S (May 1960). It was proposed that the iron particles could be alloyed with the proper choice of radioactive element, or that they could be coated with an adsorbed layer of a therapeutic agent. Later Meyers et al suggested the use of carbonyl iron particles as vehicles for site specific delivery of chemotherapeutic agents. Amer. J. Roentg., 90, 1068-1077 (Nov. 1963). Magnetic iron particles of 1 to 3 microns in diameter were shown to be localized in the vessels or gastrointestinal tract of dogs with a magnetic field of approximately 5,000 gauss. It appeared that some of the particles had been pulled through the artery into the tissues by the magnetic field. However, the surface properties of magnetic particles, such as carbonyl iron, lead to irreversible intravascular clumping upon exposure to a magnetic field unless they are coated with electronegative polymer such as albumin. Nakamura et al; J. App. Phys. 42, 1320-1324 (1971). Alksne et al, Surgery, 60, 212 (1966) employed carbonyl iron microspheres to occlude intracranial aneurysms in both animals and humans, thereby utilizing the "clumping" phenomenon for a therapeutic purpose. In 1973, Mosso et al reported an improved method for clumping particles by the use of ferromagnetic silicon which they used for selective vascular occlusion and subsequent necrosis of tumors in humans Ann. Surg., 178:5, 663 (1973). The prior art does not provide a solution to the problem of how accurate magnetic direction of intravascularly administered magnetic particles can be obtained, nor to the equally difficult problem of how sufficient loading of the chemotherapeutic agent per particle can be obtained.

Microcapsules containing magnetic particles are disclosed in U.S. Pat. No. 2,971,916. Microcapsules of 3 to 150 microns in diameter are formed by coacervation, the capsules having walls of hardened organic colloid material enclosing an oily liquid containing a dispersion of magnetic powder. No medical application is suggested, the capsules being indicated as useful for imprinting of data on record sheets.

SUMMARY OF INVENTION

The intravascularly-administrable, magneticallylocalizable biodegradable carrier of the present invention comprises microspheres formed from an amino acid polymer matrix, with magnetic particles embedded therein. For example, albumin can be used as the matrix material and magnetite ($Fe_3O_4$) as the magnetic particles. The microspheres have an average size of less than 1.5 microns and the magnetic particles have an average size of not over 1,000 Angstroms. The microspheres may contain from 5 to 350 parts by weight of the magnetic particles per 100 parts of the amino acid polymer. The therapeutic or diagnostic agent, which may be a water-soluble chemotherapeutic agent, is dissolved in or dispersed in the matrix material during the formation of the microspheres.

For effective magnetic control, the microspheres wil be introduced into an artery upstream of the capillary bed where they are to be localized, the selected capillary bed being associated with the target site. It is therefore of critical importance that the microspheres have a degree of magnetic responsiveness which permit them to pass through the arteries without significant holdup under the applied magnetic field while being immobilized and retained in the capillaries. The present invention achieves this objective by utilizing the difference in flow rates of the blood in the larger arteries and in the capillaries. In addition, the albumin surface prevents clump formation, thus allowing relatively normal blood perfusion at the area of retention. Prior to the present invention it had not been recognized or demonstrated that such discrimination in magnetic responsiveness could be obtained.

With respect to the circulatory system, mean flow velocity may be defined as the volume of blood flow through an artery, capillary, or vein divided by the cross-sectional area of the vessel. In large arteries, the velocity is of the order of 30 cm/sec, while in smaller arteries it may range from about 10 to 20 cm/sec. In veins, the flow capacity is of the order of 15 cm/sec. In contrast to the flow rates in veins and arteries, the blood flow rate in capillaries is of the order of 0.05 cm/sec. By means of a standardized test apparatus, it was demonstrated that with an ordinary permanent bipolar magnet producing a field of 8,000 gauss the difference in arterial and capillary flow rates could be used to achieve carrier retention at the desired flow of 0.05 cm/sec while permitting passage at higher flow rates. This permits the magnetic field to be applied at the time of the intra-arterial administration, assuring that the microspheres will be caught in the target capillary bed without at the same time immobilizing any substantial amount of the administered microspheres in the larger arteries. The microspheres carrying the therapeutic or diagnostic agent will therefore pass rapidly through the artery into which they are administered to the target capillary bed where they will be caught and retained, thereby effectively concentrating the agent at the target site. While being retained in the capillary bed, if desired, the applied magnetic field can be increased in strength, causing the microspheres of 0.5–1.5 microns to be drawn through the capillary walls into the tissue, and thereby retained at the target site after the magnetic field is removed. Alternatively, the applied magnetic field can hold the microcapsules at the capillary site until proteolytic enzyme action dissolves the amino acid polymer sufficiently to release the therapeutic or diagnostic agent. Further, the release rate can readily be controlled by hardening techniques to be described below.

With microspheres prepared in accordance with the present invention, at least 90% of the microspheres will be immobilized by a magnetic induction of 8,000 gauss when an aqueous suspension of the microspheres is pumped at a rate of 0.05 cm/sec. through a conduit of 0.168 cm internal diameter, but not over 10% of the microspheres will be immobilized by the same magnetic induction when pumped through the conduit at a flow rate of 10 cm/sec. or greater. The details with respect to this standardized test procedure are set out subsequently.

The microcapsules may contain the magnetic particles uniformly distributed throughout the matrix material. However, it has been discovered in connection with the present invention that greater magnetic responsiveness is obtained when the magnetic particles are concentrated in the peripheral portions of the microspheres. Such microspheres are therefore preferred though microspheres with distributed iron are not excluded. The same size microspheres can thereby contain less of the magnetic particles and relatively more of the matrix material, which is the carrier for the therapeutic or diagnostic agent. In effect, therefore, the microspheres can be more highly loaded with the active agent.

THE DRAWINGS

In the accompanying drawings, FIG. 1 is an electron photomicrograph of the preferred form of the carrier in which the magnetic particles are concentrated in the peripheral portions of the microspheres;

FIG. 2 is an illustration of a test apparatus which can be used to test the magnetic responsiveness of the microspheres; and FIG. 3 is a fragmentary enlarged view of a portion of the apparatus of FIG. 2 wherein the microspheres are subject to a standardized magnetic field.

DETAILED DESCRIPTION

The matrix material for forming the microspheres is an amino acid polymer. Such polymers are biodegradable by proteolytic enzyme action. Usable amino acid polymers include natural amino acids (proteins) and synthetic amino acid polymers. The preferred polymer is albumin, which may be animal or human albumin, but is preferably human serum albumin. Other watersoluble proteins such as hemoglobin can be substituted for albumin, the preference being for human hemoglobin. Usable syntbetic amino acid polymers include poly-L-lysine and poly-L-glutamic acid. For example, a poly-L-lysine or poly-L-glutamic acid in the molecular weight range of 20,000–50,000 can be used alone or in combination with another polymer such as albumin. However, since human serum albumin is a nearly ideal material for the purpose of the present invention, there is no necessity to use other comparable amino acid polymers. At the same time, however, such amino acid polymers are within the scope of this invention.

The magnetic particles include ferri- and ferro-magnetic compounds, such as magnetic iron oxides. The preferred magnetic particles are the black oxide or iron, magnetite ($Fe_3O_4$). Carbonyl iron of appropriate size can be used instead of the $Fe_3O_4$.

It is essential that the magnetic particles be in an ultra-fine state of subdivision. The magnetic particles should have an average size of not over 1,000 Angstroms, and preferably not over 300 Angstroms. The optimum size range for producing microcapsules of less than 1.5 microns average diameter (preferably less than 1.2 microns) is from about 50 to 250 Angstroms.

Techniques are known for producing such extremely small size magnetic particles. These include fine grinding, vacuum deposition, and chemical precipitation. Fine grinding in a ball mill can be used to produce a colloidal suspension of magnetic particles. Commercially, fine powders or suspensions of $Fe_3O_4$ are available from Ferrofluidics Corporation, Burlington, Mass. The size range of the particles is from 100 to 200 Angstroms. Aqueous base suspensions of the $Fe_3O_4$ particles with or without a surfactant can be used, but it is preferred to employ surfactant-free magnetic particles, such as $Fe_3O_4$ in a dispersed homogeneous suspension or in a dry powder form.

The carrier of this invention can be used for administering a wide variety of therapeutic or diagnostic agents. The agent may be incorporated in the amino acid polymer as a powder, or if water-soluble, in the form of a water solution. The carrier of this invention is believed to be of particular value for administering water-soluble chemotheropeutic agents, such as anti-cancer agents whose use is now limited because of adverse side effects. Heat-labile therapeutic agents can be used such as natural products since the microcapsules can be prepared at temperatures where the therapeutic agent is stable.

In general, the basic process used for forming the microspheres is known in the art. For example, the procedure described by Kramer or modifications thereof can be used. See J. Pharm. Sci., 63, 1646 (Oct. 1974); and see also Scheffel et al, J. Nucl. Med., 13, 498 (1972). The chemotherapeutic agent is dissolved in a water solution of human serum albumin and emulsified with a vegetable oil. The emulsion is added with constant stirring to a larger body of the oil held at an elevated temperature. The size of the microcapsules depends on the fineness of the emulsion, and size reduction can be obtained by procedures such as homogenization or sonication. The microcapsules are heat-hardened by partial denaturation of the albumin in the hot oil. Zolle in U.S. Pat. No. 3,937,668 describes a procedure for preparing drug-containing albumin microspheres. The substance to be incorporated is mixed in the form of a powder or precipitate with the aqueous solution of albumin, which is injected into a body of oil. Hardening of such microcapsules by techniques other than denaturation of the protein are known, and include particularly treatment of the microcapsules with aqueous formaldehyde as a hardening agent. See Madan et al, J. Pharm. Sci. 65, 1476 (Oct. 1976), and U.S. Pat. No. 2,800,457 and 3,265,629.

In practicing the present invention, from 5 to 350 parts by weight of the magnetic particles can be employed per 100 parts of the amino acid polymer. This will result in microcapsules containing corresponding proportions of the matrix material and magnetic particles. The preferred amount of magnetic material is from 10 to 150 parts by weight per 100 parts of the amino acid polymer. The amount of the therapeutic or diagnostic agent can vary over a wide range, depending on the purpose for which the microcapsules are to be used. However, in general, for water-soluble chemotherapeutic agents, from 1 to 20 parts by weight of the agent can be incorporated per 100 parts by weight of the matrix material. It will be understood, however, that the relative proportions of the therapeutic or diagnostic agent to the matrix material are not critical.

In preparing the microcapsules, an aqueous solution or dispersion of the matrix material is prepared, which can be formed into microspheres. The amount of matrix material to be used will usually be within the range from 5 to 50 parts by weight of the matrix material per 100 parts of water. With albumin and similar matrix materials preferred proportions are from 20 to 30 parts per 100 parts of water. Where a water-soluble therapeutic agent is being incorporated, it may be dissolved in the water of the matrix material solution, either before or after preparing the matrix solution.

The aqueous solution of the matrix material containing the therapeutic or diaganostic agent, either dissolved or in particulate form, is emulsified with an oil, which is preferably a vegetable oil, such as cottonseed oil, peanut oil, or the like. The aqueous phase at the time of addition of the oil will also contain the magnetic particles, which were previously added to the aqueous solution of the matrix material and dispersed therein. The proportions of the aqueous phase to the oil phase can conveniently range from about 1 to 5 parts by weight of the aqueous phase per 100 parts of the oil phase. This provides separation of the oil droplets, and prevents coalescence of the droplets in forming the microspheres. The water-in-oil emulsion is then treated to reduce the size of the dispersed droplets. Procedures such as homogenization, sonication, or both can be used. The completed emulsion should contain dispersed water droplets of an average size of less than 1.5 microns and preferably of an average size of less than 1.2 microns, corresponding to the desired size of the microspheres.

The emulsion is then added to a larger body of oil, which is preferably the same oil used to form the emulsion. In practice, cottonseed oil has been found to give good results. To promote the separation of the water droplets, the emulsion can be added in small increments to the oil bath, such as by dropwise addition. Preferably, also, the addition is accompanied by rapid stirring of the oil into which the emulsion is being introduced.

Where the therapeutic or diagnostic agent contained in the emulsion is not heat sensitive, the oil bath into which the emulsion is introduced can be heated to a temperature at which the matrix material, such as albumin, is partially denatured and hardened. For maximum hardening, temperatures in excess of 100° C. can be used, such as temperatures ranging from about 125° to 175° C. A lesser degree of hardening and denaturation can be obtained at temperatures within the range from 50° to 100° C. Where heat-hardening is employed, no chemical treatment is needed to harden the microspheres.

For incorporation of water-soluble heat-labile chemotherapeutic agents in the microspheres, it has been found that the process can be carried out at essentially room temperature. The body of oil into which the emulsion is introduced can be maintained at a temperature at which there is no inactivation of the chemotherapeutic agent, such as a temperature in the range of 1° to 45° C. Usually, it will not be necessary to either heat or cool the body of oil, using an essentially ambient temperature, such as a temperature ranging about from 20° to 30° C.

It has been found that although there is no heat-denaturation of the matrix material, such as albumin, the microspheres after introduction into the oil bath will maintain morphology and integrity as separate microspheres in a non-water miscible organic solvent, such as diethyl ether, ligroin, benzene, hexane, petroleum ether, and the like. The oil may be removed by washing with the organic solvent, such as diethyl ether, and the microspheres suspended in the organic solvent for further processing. The organic solvent can be removed by centrifugation and/or evaporation, and the resulting microcapsules dried, preferably by lyophilization. The resulting product has a relatively rapid drug release rate in water or blood, but the lyophilized microspheres if not subjected to proteolytic enzyme action will continue to retain and release a water soluble agent over periods up to 48 hours.

Where a slower release rate is desired, and particularly where greater resistance to proteolytic enzyme degradation is needed, the microspheres after being formed and before drying can be treated with a cross-linking agent for the amino acid polymer. Hardening of amino acid materials such as albumin can be accomplished, as is known in the art, by treatment with a glyoxal or aldehyde. Specific reagents include dimethyl glyoxal, glyoxal, diphenyl glyoxal, formaldehyde, 2,3-butanedione, and similar aldehydes. The glyoxal or aldehyde is preferably soluble in the organic solvent used to wash the microcapsules free of oil. For example, the organic solvent can contain a concentration of 0.2% to 20% by weight of the cross-linking agent, and may be contacted with the microspheres after or during the removal of the oil for from 5 to 120 minutes, depending on the degree of cross-linking desired. In general, the greater the amount of cross-linking, the slower will be the release rate for the water-soluble chemotherapeutic agent.

After completion of the cross-linking step, the microspheres can be washed free of excess cross-linking agent with a suitable organic solvent, as described above, such as diethyl ether, the residual solvent evaporated, and the microspheres dried, such as by lyophilization.

Formaldehyde is a particularly desirable cross-linking agent, but is generally available commercially only as a water solution, such solutions contain from 4 to 37% by weight formaldehyde. Although formaldehyde is preferentially water soluble, it can be transferred to an organic solvent, such as the solvents described above, by adding a salt to the water solution. Ammonium sulfate can be used for this purpose at a concentration in the aqueous formaldehyde of about 60 to 80% by weight. The organic solvent containing the transferred formaldehyde can then be used for treating the microspheres to cross-link the matrix material.

As will be discussed in further detail and illustrated by the foregoing examples, the carrier micrspheres prepared in accordance with this invention are capable of being immobilized at the rate of blood flow in capillaries while not being retained in the arteries to which they are introduced under the same magnetic field, the difference in magnetic responsiveness or retention being due to the difference in blood flow rates between arterial and capillary flow. For the purposes of the present invention, at least 90% of the microspheres should be immobilized by a magnetic induction of 8,000 gauss when an aqueous suspension of the microspheres is pumped at a rate of 0.05 cm/sec. through a conduit of 0.168 cm internal diameter. However, not over 10% of the microspheres should be immobilized by the same magnetic induction when pumped through the same conduit at a flow rate of 10 cm/sec. or greater. Preferably, at least 90% of the microspheres are immobilized by the described procedure at a flow rate of 0.05 cm/sec. but not over 5% of the microspheres are immobilized at the flow rate of 10 cm/sec. As will be described and further illustrated in the examples, for test purposes the magnetic induction is applied by a bipolar magnet with its poles equidistant from the centerline of the tube through which the suspension is being pumped, and the 8,000 gauss field is referenced to a plane intersecting the tube at right angles to the direction of flow and extending for at least 1.0 centimeters (cm) in the direction of flow.

For further details, reference should be made to the following examples.

EXAMPLE I 125 mg human serum albumin, 10 mg bulk purified adriamycin HCl, and 36 mg $Fe_3O_4$ powder (200 A average particle size) was placed in a 50 ml beaker and dissolved and suspended respectively in 0.5 ml distilled water. For experimental purposes, the albumin may be trace labeled with 0.1 mg $^{125}$I-bovine-serum-albumin. The suspension was stirred well to evenly disperse the $Fe_3O_4$ in the albumin-adriamycin solution, but no surfactant was employed to aid the dispersion. Next 30 ml of cottonseed oil was added to the suspension forming a water-in-oil emulsion, which was then stirred well to disperse the aqueous phase into the oil.

The resultant emulsion was homogenized by sonication (Branson Sonifier Model 185) at 100 watts for one minute at 4° C. Next, the homogenate was added dropwise into 100 ml of cottonseed oil at 25° C. being constantly stirred at 1800 RPM for 10 minutes to fully disperse the emulsion.

The oil was then removed by washing 4 times in 60 ml diethyl ether anhydrous and centrifuged at 2000×g for 30 minutes. After the fourth wash the oil free microspheres were then hardened by a formaldehyde 1% w/v solution in 100 ml ether (8 mg microspheres/ml ether-formaldehyde solution). The ether-formaldehyde solution was prepared by transferring aqueous formaldehyde to the ether phase by shaking a 1:5 (37% aqueous formaldehyde:ether) solution in the presence of saturating ammonium sulfate. The amount of formaldehyde transferred at this ratio was determined in a separate study using tritium labeled formaldehyde (1.5 mCi/1.5 mg) as a trace label in the 37% aqueous solution. The hardening was accomplished by dispersing the washed microspheres in the formaldehyde/ether and stirring at 100 RPM for the desired time (5 min to 2 hrs), depending on the extent of hardening desired. After hardening was terminated, the formaldehyde cross-linking reagent was removed by centrifugation in ether, four times. Any remaining ether was allowed to evaporate and the resultant material was further processed by lyophilization, and then stored at 4° C.

The microcapsule product contained approximately by weight 21% $Fe_3O_4$, 73% albumin, and 5% adriamycin. Examination by immersion fixation-transmission electron microscopy confirmed that the microcapsules were generally spherical in shape and of an average size of about 1 micron. The appearance of the microcapsules is shown in FIG. 1 (Transmission E.M. Mag.=X28,000).

The fixation and processing procedures used for the electron microscopy were as follows:

The microspheres were placed in paraformaldehyde-glutaraldehyde for 0–2 hrs. They were then washed in cacodylate buffer, dehydrated in a graded series of alcohols and embedded in Epon 812. Thin sections were stained with uranyl acetate followed by lead citrate. Thick sections were stained with toluidine blue.

Referring to FIG. 1, it will be noted that there are a few aberrant microcapsules (A) which are non-spherical. However, the general uniformity of the microcapsules with respect to both shape and size distribution is evident. Some of the microcapsules appear to contain relatively large vacuoles (V), but most appear to have substantially solid albumin matrices (C).

The magnetic iron particles (P) of $Fe_3O_4$ are concentrated in the peripheral portions of the microspheres. No particle-dispersing surfactant was used in preparing these microcapsules. When the $Fe_3O_4$ is incorporated in the microcapsules in the form of an aqueous suspension containing the surfactant, the magnetic particles tend to disperse throughout the microcapsules relatively uniformly.

EXAMPLE II

The procedure for preparing the microspheres was identical to that of Example I except that 135 mg $Fe_3O_4$ was used instead of the 36 mg of Example I. The microcapsule product contained approximately by dry weight 50% $Fe_3O_4$, 4% adriamycin, and 46% albumin.

EXAMPLE III

Microcapsules were prepared by the identical procedure of Example I, using approximately the same amount of $Fe_3O_4$ as in Example II. The $Fe_3O_4$ was in the form of an aqueous suspension containing a surfactant, aqueous base Ferrofluidics $Fe_3O_4$ Catalog No. A-01, 400 gauss saturation (Ferrofluidics Corporation, Burlington, Mass.). 0.3 ml of the A-01 product was added, containing approximately 130–140 mg $Fe_3O_4$. The average $Fe_3O_4$ particle size was in the range of 150–200 Angstroms. The microcapsular product contained approximately by dry weight 51% $Fe_3O_4$, 4% adriamycin, and 45% albumin.

EXAMPLE IV

The procedure of Example I was followed except that the homogenate was added to 100 ml of preheated oil (135° C.) for 10 minutes. Washing is as described previously, but the aldehyde hardening is omitted. The rest of the procedure is the same.

EXAMPLE V

A. Same procedure as Example I except microspheres are not hardened by a cross-linking agent or by heat. The oil bath is at a temperature of 20°–25° C. After the oil has been washed away with diethyl ether anhydrous 4 times, the spheres are air dried, then lyophilized and stored at 4° C.

Stability of the resultant microspheres was tested as follows: First, 5 microliters of $^{125}$I-bovine serum albumin (New England Nuclear, 1.51 mCi/mg) was added in the initial homogenate to trace label the microspheres. An aliquot of the resultant microspheres was then suspended and sonicated for 2 minutes in 0.154 M NaCl-0.1% Tween 80 and incubated at 37° C. for 24 and 48 hours. After this period of time, the suspension was centrifuged at 2000×g for 10 minutes and the supernatant and pellet were counted in a gamma counter. The number of counts obtained in the supernatant (after subtracting free label) was divided by the total number of counts was regarded as the percentage breakdown of the carrier (non-pelleting). Only 16% of the microspheres had deteriorated after 24 hrs. and 37% after 48 hrs. With formaldehyde or heat-hardening less than 3% deterioration occurs in 48 hrs.

B. Same procedure as Example I except 3,400 units of urokinase was added to the 125 mg of HSA omitting the $Fe_3O_4$ and adriamycin. No cross-linking was done in this experiment.

Two mg of the resultant microspheres were placed into 16 12×75 mm tubes for duplicate time course of 0, 15, 30, 60 minutes; 2, 4 and 6 hours. At the appropriate time, microspheres were suspended in sodium barbital buffer (0.05 M) and left at room temperature. Finally at zero time all tubes were centrifuged at 3,500 RPM (1900×g) for 15 minutes at 4° C. and 25 microliters of the supernatants were pipetted into appropriate wells on fibrin-agar plates. Plates were then read 4 and 6 hours later for fibrinolysis (i.e. diameters).

It was found that 60% of maximum lysis was seen after 10 minutes on fibrin-agar plate.

Other Examples

As a variation of the procedure of Example I, 2,3-butanedione (5% v/v in anhydrous ether) or butyraldehyde (10% v/v in anhydrous ether) is employed as a cross-linking agent, the contact time ranging from 5 minutes to 2 hours. The product is recovered and dried as described in Example I.

As a further variation of the procedure of Example I, 20 mg of poly-L-lysine or polyglutamic acid is combined with the 125 mg of human serum albumin. The rest of the procedure is identical. In another modification, hemoglobin is substituted on an equal weight basis for the albumin.

Determination of Magnetic Responsiveness

The magnetic responsiveness of the microspheres under varying liquid flow rates was studied under standardized conditions, using the apparatus of FIG. 2. The apparatus included a container 10 providing a reservoir containing an aqueous fluid. Normal saline was used. A pick-up tube 12 connects the reservoir through a three-way valve 13 with a syringe 14, the plunger 15 of which is driven by the pusher block 16 of a variable speed syringe pump 17. The syringe pump was Model 314, manufactured by Sage Instruments Division, Orion Research Incorporated, Cambridge, Mass. The on-off switch is indicated at 18 and the variable speed selector at 19. Since the construction and operation of such syringe pumps are well known, it will not be necessary to describe the pump mechanism herein.

Using the 50 cc syringe employed for the tests, the syringe pump had a low and high setting range which permitted the flow rate through the measurement tube of the apparatus to be varied over the range from 0 to 10 cm/sec with a measurement tube internal diameter of 0.168 cm. During the discharge of the liquid from syringe 14, plunger 15 moves in the direction of the arrows as shown in FIG. 2, the liquid flowing through outlet nipple 20, connecting tube section 21, and valve 13 to supply conduit 22, which connects through on-off valve 23 to sample injector 24. As shown, injector 24 includes an injection chamber 25 of downwardly-converging cross-section, the lower end of which communicates with the liquid-flow passage 26. The upper end of chamber 25 is closed by a rubber diaphragm stopper 27 through which the needle of a hypodermic injection syringe 28 can be inserted.

A guide tube 29 is attached to a nipple extension at the lower end of injector passage 26. Inserted within guide tube 29 is a removable and replaceable measurement tube 30. A series of such tubes are used. The measurement tube fits snugly within the guide tube so that the flow of liquid is through the measurement tube. Preferably, the guide tube is formed of relatively rigid material, such as plastic or glass, and the measurement tubes are formed of flexible plastic tubing such as polyethylene. For the purposes of the standardized measurements, which define the magnetic responsiveness of the microcapsules under different liquid flow conditions in accordance with the present invention, the internal diameter of the guide tube should be 0.168 cm. (cross-section 0.0222 cm$^2$).

Intermediately between the upper and lower ends of guide tube 29 and measurement tube 30, there is located a bipolar magnet designated generally by the number 31. As indicated, the poles of magnet 31 should be equidistant from the centerline of the tubes 29, 30. An adjustable gap permanent U-magnet can be used capable of generating a magnetic induction in the range of 7500–8500 gauss with a pole spacing permitting straddling of the guide tube. In the tests described herein, the magnet was Model No. 70,810 Adjustable Gap Permanent Magnet, Edmund Scientific Co., Barrington, N.J., having ½ inch width pole faces (1.27 cm.). In FIG. 2 the complete magnet is not illustrated, but only the adjustable pole shoes 31a and 31b. The flat ends of these shoes are the pole faces. By varying the spacing between the inner ends of the pole shoes the magnetic induction can be selectively varied. The pole shoes were adjusted to a separation of approximately 3/16 inches and until a magnetic induction of 8,000 gauss was obtained. The measured 8,000 gauss magnetic field for standardization purposes is referenced to a plane intersecting the measurement tube 30 at right angles to the direction of flow through the tube. Measurement of the magnetic induction was made with Bell Model 600 Gauss meter using a transverse probe (F. W. Bell, Inc., Columbus, Ohio). These measurements indicated that the 8,000 gauss field was substantially uniform between the opposed parallel ends of the magnet shoes 31a, 31b, as represented by the distance x. The extent of the magnetic field along the direction of flow is not critical, providing the flow-direction of the field is sufficient to permit the magnetic force to act on the microcapsules. For purpose of standardization, it is specified that the referenced 8,000 gauss field should extend for at least 1.0 cm (10 mm) in the direction of flow (the distance "x"). To avoid any inaccuracy due to acceleration effects, the upper end of the measurement tube 30 should extend above the area of the magnetic field, such as by the distance "y". This distance is not critical, but in practice it was found that a 20 cm extension of the tube was satisfactory. However, greater or lesser extensions can be used.

Conveniently, a clamp may be used for closing the projecting lower end of measurement tube 30 after the completion of a measurement run, such as hemostat clamp 32. It will be understood that a series of the measurement tubes 30 will be used, as well as a series of sample collection containers 33, 34.

In using the apparatus of FIG. 2, the following steps are followed:

(1) Insert measurement tube 30 in guide tube 29, as shown in FIG. 2.

(2) With valve 23 in the off position, turn valve 13 to connect tube 12 to the syringe 14 using a 50 cc syringe.

(3) Fill the syringe with the fluid from the reservoir, plunger 15 and pusher 16 moving to their outermost positions.

(4) Turn valve 13 to connect syringe 14 with tube 22, and open valve 23.

(5) Start pump 17 to fill tube 22, injector 24 (except for a small air space below diaphragm 27), the upper end of guide tube 29, and measurement tube 30.

(6) Stop pump 17 and close valve 23.

(7) Inject bolus of microspheres to be tested with hypodermic syringe into injection chamber 28 of injector 24. A 0.1 ml. bolus was used, but this can be varied.

(8) Open valve 23 and start pump 17, the rate of travel of pusher 16 having been selected in relation to the 50 cc size of syringe 14 to give a selected uniform flow rate through the 0.168 cm I.D. sample tube (e.g. 0.05 cm/sec, etc.).

(9) The flow of the water carrier (normal saline) aspirates the microspheres from the injection chamber 25 into the liquid stream passing between the poles of the magnet 31.

(10) The flow is continued until all of the magnetic material has been removed from the injection chamber and has either collected within the section of the measurement tube subject to the magnetic field, or has passed with the flowing liquid into the first collection vessel 33. The retained or immobilized microspheres are indicated in FIG. 3.

(11) For each sample, the test can be repeated at different flow rates such as 0.05 cm/sec and 10 cm/sec to determine the difference in magnetic retention. The nonretained fraction collected first in container 33 includes the microspheres that are not immobilized by the magnetic field at the particular flow rate.

(12) The syringe pump is turned off, valve 23 closed, and the lower end of sample tube 30 is clamped or otherwise closed.

(13) The sample tube is withdrawn, and the liquid is drained into a second sample collection vessel 34. To eliminate possible error due to microspheres remaining within the tubing 30 after draining, it is cut up and added to the liquid, as indicated in FIG. 2.

(14) The microsphere content of the two samples is measured conveniently by using trace labeled microspheres (e.g. $^{125}$I-albumin) and a gamma counter. (See Example I.)

In the test results reported below, a bolus of 0.1 ml of the magnetic microspheres (1 mg/ml) trace labeled with $^{125}$I-albumin ($4 \times 10^4$ CPM/mg microspheres) was employed, the carrier liquid being 0.9% saline containing 0.1% Tween 80. The injection was 20 cm upstream of the zone of the magnetic field. The counting of the non-retained and retained fractions was made with a Packard Model 578 well-type gamma counter. The amount retained was then calculated as a percent of the total (retained fraction plus non-retained fraction). Reproduceability was found to be ±2% with at least two determinations of each measured value. In the operation of the test apparatus, it will be understood that the liquid flow should be laminar and uniform.

The comparison of trace-labeled samples of microspheres, prepared as described in Examples I and II, is summarized below in Table A. The data demonstrates that magnetic retention varies reproducibly with flow rate, and shows that over the range from 0.05 to 10 cm/sec that the retention can be varied from substantially complete to substantially no retention. For the microspheres containing 21% $Fe_3O_4$ and flowing at 0.05 cm/sec, 99% were retained, but only 0.2% at 9.8 cm/sec. The microspheres containing 50% $Fe_3O_4$ (dry weight basis) were 99% retained at 0.05 cm/sec, but only 8–10.7% retained at flow rates of 6.60–9.80 cm/sec.

Table B as set out below represents a comparison of magnetic responsiveness of the microspheres prepared in Example II with those of Example III. The microspheres are of the same size (average 1 micron diameter) and contain approximately the same amount of magnetic iron (50–51%) but the magnetic particles are differently distributed. With peripheral type distribution greater magnetic responsiveness is obtained. This makes it possible to use a lesser proportion of the magnetic particles in relation to the matrix material, permitting larger amounts of a therapeutic agent to be incorporated with the matrix material in the same size microspheres.

TABLE A

Retention of Microspheres at 8,000 Gauss

| Velocity (cm/sec) | % Retention | |
|---|---|---|
| | 21% $Fe_3O_4$ | 50% $Fe_3O_4$ |
| 0.05 | 97.0 | 99.0 |
| 0.20 | 85.3 | 98.0 |
| 0.50 | 66.5 | 94.6 |
| 0.70 | 56.2 | 91.9 |
| 1.00 | 40.1 | 78.3 |
| 1.60 | 24.2 | 66.0 |
| 2.30 | 19.2 | 51.0 |
| 3.30 | 9.6 | 40.1 |
| 5.00 | 6.1 | 16.3 |
| 6.60 | 5.3 | 8.0 |
| 9.80 | 0.2 | 10.7 |

TABLE B

Comparison Magnetic Responsiveness of Microspheres with Peripheral and Dispersed Magnetic Material (50–51% $Fe_3O_4$)

| Velocity (cm/sec) | % Retention | |
|---|---|---|
| | Dispersed | Peripheral |
| 0.05 | 99.0 | 99.3 |
| 0.20 | 98.0 | 99.5 |
| 0.50 | 94.6 | 95.4 |
| 0.70 | 91.9 | 89.9 |
| 1.00 | 78.3 | 88.1 |

TABLE B-continued

Comparison Magnetic Responsiveness of Microspheres with Peripheral and Dispersed Magnetic Material (50–51% Fe₃O₄)

| Velocity (cm/sec) | % Retention Dispersed | % Retention Peripheral |
|---|---|---|
| 1.60 | 66.0 | 83.1 |
| 2.30 | 51.0 | 71.0 |
| 3.30 | 40.1 | 58.0 |
| 5.00 | 16.3 | 35.6 |
| 6.60 | 8.0 | 29.1 |
| 9.80 | 10.7 | 10.4 |

IN VIVO TESTS

Microspheres containing approximately 21% $Fe_3O_4$ were prepared as described in Example I using trace labeled albumin.

The microspheres were tested in vivo. The model chosen, based on ease of manipulation and access, was the central caudal artery in the tail of the rat. The animals used were 400 gram female retired breeder rats. The artery was partially exposed at the base of the tail and a polyethylene catheter presoaked in a 0.6% heparin 1000 in saline solution was inserted caudally 4 cm. A permanent bipolar magnet with a field strength of 8000 Oe was placed 7 cm caudally from the point of insertion of the catheter. Varying amounts of microspheres, suspended in 0.1% Tween 80 in 0.9% NaCl, were infused by a constant flow syringe pump (Sage, Model 341) at 0.06 ml/min which corresponds to the blood flow rate of this artery previously determined. After infusion the catheter was removed and the magnet was retained in position for thirty minutes. A transcutaneous Doppler apparatus (Parks Electronics Lab, Model 881-A) was used to verify resumption of blood flow following removal of the catheter from the artery. After the thirty minute period, the rat was sacrificed via intracardiac injection of saturated KCl and the organs were removed and counted for $^{125}$I activity in a Packard (Model 578) gamma counter. The tail was cut into four equal sections, and each section was counted individually. Results of this study are shown in Table C. Multiple animals for each field strength were used to determine the average $^{125}$I-magnetic-microsphere body distribution.

In a modification of the foregoing procedure, the animals were sacrificed 24 hours after removing the tail from the magnetic field. Once again, 50% of the injected counts were found at the target site. This phenomenon, as well as the carrier distribution in the skin, suggests the possibility that the carrier is lodging in the vascular endothelium or possibly traversing the vascular basement membrane into interstitial tissue due to the magnetic force applied. This phenomenon would be extremely desirable as the microspheres would act as extra vascular depots releasing the drug at a fixed rate at a desired target site.

An additional animal model was chosen to illustrate carrier localization. In this study the carrier was localized to the lungs of $BDF_1$ female mice. A modification of the above procedure for introduction of the carrier consisted of tail vein injection rather than catheterization, and the use of a unipolar magnet instead of a bipolar to generate the field. Thirty minutes following injection, the mouse was sacrificed and the organs counted for $^{125}$I activity as described above In the experimental animals, 45–50% of the total counts injected were found in the lung as compared to 6–12% of the counts found in control animal lungs.

TABLE C

Average Percent Distribution of [125]I-Magnetic Microspheres

| MAGNETIC FIELD GAUSS | TAIL SECTION 1 | 2 | 3 | 4 | ORGAN Liver | Spleen | Kidney | Lung | Heart |
|---|---|---|---|---|---|---|---|---|---|
| No Field | 0 | 0 | 0 | 0 | 80 | 10 | <1 | 10 | 0 |
| 4000 | 0 | 0 | 3 | 0 | 85 | 7 | <1 | 5 | 0 |
| 6000 | 0 | 0 | 19 | — | 57 | 8 | <1 | 12 | 0 |
| 8000 | 0 | 1 | 50 | 0 | 39 | 4 | <1 | 7 | 0 |

We claim:

1. An intravascularly-administrable, magnetically-localizable biodegradable carrier, comprising microspheres formed from an amino acid polymer matrix with magnetic particles embedded therein, said microspheres having an average size of less than 1.5 microns and said magnetic particles having an average size of not over 1,000 Angstroms, said microspheres containing from 5 to 350 parts by weight of said magnetic particles per 100 parts of said amino acid polymer, at least 90% of said microspheres being immobilized by a magnetic induction of 8,000 gauss when an aqueous suspension of said microspheres is pumped at a rate of 0.05 centimeters per second through a conduit of 0.168 centimeter internal diameter but not over 10% of said microspheres being immobilized by said magnetic induction when pumped through said conduit at a flow rate of 10 centimeters per second, said magnetic induction being applied by a bipolar magnet with its poles equidistant from the centerline of said tube, said 8,000 gauss being referenced to a plane intersecting said tube at right angles to the direction of flow and extending for at least 1.0 centimeter in the direction of flow.

2. The carrier of claim 1 in which said magnetic particles are concentrated in the peripheral portions of said microspheres.

3. The carrier of claim 1 in which said microspheres contain from 10 to 150 parts by weight of said magnetic material per 100 parts of said amino acid polymer.

4. The carrier of claim 3 in which said magnetic material is $Fe_3O_4$ and said amino acid polymer is albumin.

5. An intravascularly-administrable, magnetically-localizable biodegradable carrier, comprising microspheres formed from an amino acid polymer matrix with magnetic particles embedded therein, said microspheres having an average size of less than 1.2 microns and said magnetic particles having an average size of not over 300 Angstroms, said microspheres containing from 10 to 150 parts by weight of said magnetic particles per 100 parts of said amino acid polymer, at least 95% of said microspheres being immobilized by a magnetic induction of 8,000 gauss when an aqueous suspension of said microspheres is pumped at a rate of 0.05 centimeters per second through a conduit of 0.168 centimeters internal diameter but not over 5% of said microspheres being immobilized by said magnetic induction when pumped through said conduit at a flow rate of 10 centimeters per second, said magnetic induction being applied with a bipolar magnet with its poles equidistant from the centerline of said tube, said 8,000 gauss being referenced to a plane intersecting said tube at right angles to the direction of flow and extending for at least 1.0 centimeter in the direction of flow.

6. The carrier of claim 5 in which said magnetic particles are concentrated in the peripheral portions of said microspheres.

7. The carrier of claim 5 in which said magnetic material is $Fe_3O_4$ and said amino acid polymer is albumin.

8. An intravascularly-administrable, magnetically-localizable biodegradable carrier, comprising microspheres formed from albumin with particles of $Fe_3O_4$ embedded therein, said microspheres having an average size of less than 1.2 microns and said magnetic particles having an average size of not over 300 Angstroms, said microspheres containing from 10 to 150 parts by weight of said $Fe_3O_4$ particles per 100 parts of said albumin, at least 95% of said microspheres being immobilized by a magnetic induction of 8,000 gauss when an aqueous suspension of said microspheres is pumped at a rate of 0.05 centimeters per second through a conduit of 0.168 centimeters internal diameter but not over 5% of said microspheres being immobilized by said magnetic induction when pumped through said conduit at a flow rate of 10 centimeters per second, said magnetic induction being applied with a bipolar magnet with its poles equidistant from the centerline of said tube, said 8,000 gauss being referenced to a plane intersecting said tube at right angles to the direction of flow and extending for at least 1.0 centimeter in the direction of flow.

9. The carrier of claim 8 in which said $Fe_3O_4$ particles are concentrated in the peripheral portions of said microspheres.

10. An intravascularly-administrable, magnetically-localizable biodegradable carrier, comprising microspheres formed from an amino acid polymer matrix with magnetic particles embedded therein, said microspheres having an average size of less than 1.5 microns and said magnetic particles having an average size of not over 1,000 Angstroms, said microspheres containing from 5 to 350 parts by weight of said magnetic particles per 100 parts of said amino acid polymer, at least 90% of said microspheres being immobilized by a magnetic induction of 8,000 gauss when an aqueous suspension of said microspheres is pumped at a rate of 0.05 centimeters per second through a conduit of 0.168 centimeter internal diameter but not over 10% of said microspheres being immobilized by said magnetic induction when pumped through said conduit at a flow rate of 10 centimeters per second, said magnetic induction being applied by a bipolar magnet having pole faces of 12.7 millimeters in width with said pole faces equidistant from the centerline of said tube, said 8,000 gauss being referenced to a plane intersecting said tube at right angles to the direction of flow and extending for substantially 12.7 millimeters in the direction of flow.

11. An intravascularly-administrable, magnetically-localizable biodegradable carrier, comprising microspheres formed from an amino acid polymer matrix with magnetic particles embedded therein, said microspheres having an average size of less than 1.2 microns and said magnetic particles having an average size of not over 300 Angstroms, said microspheres containing from 10 to 150 parts by weight of said magnetic particles per 100 parts of said amino acid polymer, at least 95% of said microspheres being immobilized by a magnetic induction of 8,000 gauss when an aqueous suspension of said microspheres is pumped at a rate of 0.05 centimeters per second through a conduit of 0.168 centimeters internal diameter but not over 5% of said microspheres being immobilized by said magnetic induction when pumped through said conduit at a flow rate of 10 centimeters per second, said magnetic induction being applied by a bipolar magnet having pole faces of 1.27 centimeters in width with said pole faces equidistant from the centerline of said tube, said 8,000 gauss being referenced to a plane intersecting said tube at right angles to the direction of flow and extending for substantially 1.27 centimeters in the direction of flow.

12. An intravascularly-administrable, magnetically-localizable biodegradable carrier, comprising microspheres formed from albumin with particles of $Fe_3O_4$ embedded therein, said microspheres having an average size of less than 1.2 microns and said magnetic particles having an average size of not over 300 Angstroms, said microspheres containing from 10 to 150 parts by weight of said $Fe_3O_4$ particles per 100 parts of said albumin, at least 95% of said microspheres being immobilized by a magnetic induction of 8,000 gauss when an aqueous suspension of said microspheres is pumped at a rate of 0.05 centimeters per second over 5% of said microspheres being immobilized by said magnetic induction when pumped through said conduit at a flow rate of 10 centimeters per second, said magnetic induction being applied by a bipolar magnet having pole faces of 1.27 centimeters in width with said pole faces equidistant from the centerline of said tube, said 8,000 gauss being referenced to a plane intersecting said tube at right angles to the direction of flow and extending for substantially 1.27 centimeters in the direction of flow.

* * * * *